United States Patent [19]

Cox et al.

[11] Patent Number: 5,206,015
[45] Date of Patent: Apr. 27, 1993

[54] INTRODUCTION OF BACTERIA IN OVO

[75] Inventors: Nelson A. Cox, Bogart; Joseph S. Bailey, Athens, both of Ga.

[73] Assignee: The United States of America as represented by the Secretary of Agriculture, Washington, D.C.

[21] Appl. No.: 362,635

[22] Filed: Jun. 5, 1989

[51] Int. Cl.5 .................... A01N 63/00; A61K 37/00; C12N 1/02
[52] U.S. Cl. .................... 424/93 C; 119/6.8; 119/6.6; 435/853; 424/93 J
[58] Field of Search ............. 119/1, 6.8, 6.6; 424/93, 93 C; 800/2; 435/853-857

[56] References Cited

U.S. PATENT DOCUMENTS

| | | | |
|---|---|---|---|
| 3,953,609 | 4/1976 | Farr | 426/2 |
| 4,040,388 | 8/1977 | Miller | 119/6.8 |
| 4,251,509 | 2/1981 | Hanson et al. | 424/89 |
| 4,335,107 | 6/1982 | Snoeyenbos et al. | 424/93 C |
| 4,469,047 | 9/1984 | Miller | 119/6.8 |
| 4,593,636 | 6/1986 | Miller et al. | 119/6.8 |
| 4,657,762 | 4/1987 | Mikkola et al. | 424/93 C |
| 4,681,063 | 7/1987 | Hebrank | 119/6.8 |
| 4,689,226 | 8/1987 | Nurmi et al. | 424/93 C |
| 4,903,635 | 2/1990 | Hebrank | 119/6.8 |

FOREIGN PATENT DOCUMENTS 0251750  1/1988  European Pat. Off. .

OTHER PUBLICATIONS

*Webster's II. New Riverside University Dictionary*. The Houghton Mifflin Co. 1984. p. 473.
Wilson, Jeanna L., et al., "Hatchery Sanitation Procedures after new formaldehyde use rules", Poultry Digest, Sep. 1989, pp. 406–408.
Mauldin, Josephs M., et al., "Twelve Components of a Good Hatchery Sanitation Program", Georgia Hatchery Breeders School Notebook, Dec. 1990, seven pages.
Roberts, Tanya, "The Economic Losses Due to Selected Foodborne Diseases", Ec. Res. Service/USDA, Oct. 1986, 25 pages.
Pivnick, H. and E. Nurmi, "The Nurmi Concept . . . " in Devel. in Food Microbiology, 1:41–70, 1982.
Pivnick, H. et al, "Prevention of Salmonella Infection . . . ", J. of Food Protection, vol. 44, No. 12, pp. 909–916, Dec. 1981.
Bailey, J. Stan, "Integrated Colonization Control of . . . ", Poultry Science, 1988, 67:928–932.
Bailey, J. Stan, "Factors Affecting Microbial Competitive Exclusion . . . ", Food Tech. 41, No. 7, 88–92, Jul. 1987.
Goren, E. et al, "Reduction of Salmonella Infection . . . ", The Veterinary Quarterly, vol. 10, No. 4, Oct. 1988.

*Primary Examiner*—Christopher S. F. Low
*Attorney, Agent, or Firm*—M. Howard Silverstein; John D. Fado; Joseph A. Lipovsky

[57] ABSTRACT

A method and apparatus for introducing probiotic bacteria into the digestive tract of a bird in order to exclude undesirable bacteria therefrom, and inoculated eggs produced thereby, are disclosed. In a preferred embodiment of the invention, a fertile bird egg is administered a Salmonella competitive exclusion culture. The culture is preferably administered into the air cell of the egg in an amount effective to colonize the digestive tract of the embryonic bird contained within the egg, and the culture preferably comprises at least one anaerobic bacteria of intestinal origin.

7 Claims, No Drawings

INTRODUCTION OF BACTERIA IN OVO

FIELD OF THE INVENTION

The present invention relates to methods and apparatus for introducing bacteria into the digestive tract of birds, and inoculated eggs produced thereby.

BACKGROUND OF THE INVENTION

Two million cases of Salmonella food poisoning are estimated to occur each year in the United States alone. Acute symptoms of this disorder include nausea, vomiting, diarrhea, cold chills, fever, and exhaustion. A small percentage of those afflicted (0.1%, or 2,000 people annually in the United States) die from Salmonella poisoning, with these victims usually being infants, the sick, and the elderly. See Generally T. Roberts, *The Economic Losses Due to Selected Foodborne Diseases.* 5-6 (1986) (Economic Research Service/USDA, 1301 New York Avenue, N.W., Room 1108, Washington, DC 20005-4788).

Of all potential sources of Salmonella poisoning, poultry products have been identified as the primary source. Thus, breaking the chain of salmonellae being passed from one generation of birds to the next has been the goal of poultry researchers for at least twenty-five years. However, a special type of symbiotic relationship (a commensal relationship) exists between a host bird and salmonellae living within it. Because the bird's health is not impaired by the salmonellae, it does little to exclude the organism or to try to rid itself of the organism once it has been colonized. The prevention of salmonellae colonization in poultry is therefore extremely difficult.

One approach to preventing salmonellae colonization of poultry is competitive exclusion. See generally H. Pivnick and E. Nurmi, *Developments in Food Microbiologly* 1, 41 (1982). In this approach, a probiotic bacterial culture (that is, a bacterial culture which has a beneficial effect on the animal to which it is administered) is introduced into a bird's digestive tract prior to its colonization by Salmonella. The probiotic bacterial culture is selected to occupy the same environmental niche in the bird's digestive tract that the Salmonella would occupy, so that Salmonella which subsequently pass into the bird's digestive tract tend to be excluded by the bacteria which have been purposely introduced. Competitive exclusion is a promising method of preventing Salmonella from colonizing birds which are raised in a comparatively Salmonella-free environment. Unfortunately, there are numerous potential sources of salmonellae contamination in a modern poultry operation, including chicks, feed, rodents, birds, insects, and the transportation and processing procedures to which the birds are subjected. These diverse sources of contamination make it difficult to administer a competitive exclusion culture to a bird before it is first colonized by Salmonella.

An object of the present invention is, accordingly, to provide a new technique for introducing probiotic bacteria into the digestive tracts of birds. A more particular object of the present invention is to provide a new technique for competitively excluding Salmonella from the digestive tract of birds prior to colonization by Salmonella.

SUMMARY OF THE INVENTION

A method for introducing bacteria into the digestive tract of a bird is disclosed herein. The method comprises administering a bacterial culture to a fertile bird egg (thereby administering the culture to the embryonic bird contained within the egg). The bacterial culture, which preferably comprises at least one strain of anaerobic bacteria of intestinal origin, is administered in an amount effective to colonize the digestive tract of the embryonic bird contained within the egg. Preferably, the bacterial culture is administered by depositing it in the air cell of the egg. After injection, the eggs are incubated to hatch. The digestive tracts of the hatchlings of these eggs are found to be colonized by the bacterial culture at the time of hatch.

Another aspect of the present invention is an egg injection apparatus for use in the automated injection of a bird egg (which egg contains a live embryonic bird) with an injection liquid (which includes the aforementioned probiotic bacterial culture, or consists essentially of said probiotic bacterial culture). An apparatus of the present invention may comprise: egg holder means for retaining at least one egg, and egg injector means (which contains a probiotic bacterial culture) operatively associated with the egg holder means, said egg injector means functioning to inject into each said at least one egg an amount of said probiotic culture effective to colonize the digestive tract of an embryonic bird within each said at least one egg. The injector is positioned for injecting an egg carried by the egg holder means with the probiotic bacterial culture. The egg holder means and the egg injector means may each be connected to a support frame. Preferably, the egg injector means is positioned, dimensioned and configured to inject the injection liquid into the air cell of the egg(s). The bacterial culture contained in the egg injector means preferably comprises at least one anaerobic bacteria of intestinal origin. The egg injector means is configured to deliver to the egg(s) the bacterial culture in an amount effective to colonize the digestive tract of the embryonic bird. Preferably, the apparatus also comprises punch means (which may be connected to the supporting frame) operatively associated with the egg injector means for providing a hole in the egg's shell prior to injection, through which hole a needle is inserted.

Another aspect of the present invention is a fertile bird egg having deposited therein the aforementioned probiotic bacterial culture, the bacterial culture preferably comprising at least one anaerobic bacteria of intestinal origin, the bacterial culture present in an amount effective to colonize the digestive tract of the embryonic bird contained within the egg. Preferably, the bacterial culture is deposited within the air cell of the egg.

DETAILED DESCRIPTION OF THE INVENTION

The present invention may be practiced with any type of bird egg, including chicken, turkey, duck, goose, quail, or pheasant eggs. Chicken and turkey eggs are preferred, with chicken eggs most preferred. Eggs injected by the method of the present invention are fertile eggs which are preferably in the fourth quarter of incubation. Chicken eggs are treated on about the fifteenth to eighteenth day of incubation (the eighteenth day of embryonic development), and are most preferably treated on about the eighteenth day of incubation.

Turkey eggs are preferably treated on about the twenty-first to twenty-sixth day of incubation, and are most preferably treated on about the twenty-fifth day of incubation.

Any probiotic bacterial culture capable of proliferating in the digestive tract of a bird can be employed in practicing the present invention, with the dosage delivered being adjusted as appropriate given the size of the subject. Probiotic bacterial cultures are cultures of nonpathogenic bacteria capable of inhabiting at least one region of the bird's gut. Such cultures are administered to animals for a variety of reasons, including the enhancing of digestive efficiency and the preventing of disease. See, e.g., U.S. Pat. No. 3,953,609 to Farr (the disclosure of this and all other patent references cited herein is incorporated herein by reference). Preferred are bacterial cultures which comprise at least one strain of anaerobic bacteria, these anaerobic bacteria preferably being of intestinal origin.

Preferably, the bacterial culture is one capable of excluding Salmonella from the digestive tract of a bird. Such bacterial cultures are called competitive exclusion (CE) cultures. The culture may optionally include an oxygen scavenging agent such as cysteine, as described in U.S. Pat. No. 4,657,762 to Mikkola et al. The cultures may be either defined cultures or undefined cultures, with undefined cultures currently preferred. Undefined cultures comprise, very simply, cultures of bacteria obtained from the digestive tracts of mature birds which are free of Salmonella. Such cultures are known. See H. Pivnick and E. Nurmi, supra at 49–54. While the undefined culture may be obtained from any location in a bird's digestive tract, it is preferably obtained from either the caecum or large intestine.

Defined cultures (also called pure cultures) are cultures in which the identities of the bacteria contained therein are known. Numerous defined cultures are available which can be used to practice the present invention. See, e.g., H. Pivnick and E. Nurmi, supra at 64–65. Defined cultures consisting essentially of at least four anaerobically co-cultured strains of normal alimentary tract bacterial species, the strains chosen from those normally present in the alimentary tract of poultry, with each strain selected to have an adhesion efficiency onto the epithelial cells of the alimentary tract of poultry of at least ten bacteria per cell as determined by the Fuller adhesion test, are disclosed in U.S. Pat. No. 4,689,226 to Nurmi et al. Other suitable defined cultures are disclosed in U.S. Pat. No. 4,335,107 to Snoeyenbos et al. The cultures disclosed by Snoeyenbos are mixtures of avian intestinal microflora treated to prevent the inactivation thereof, the microflora having the property of blocking subsequent colonization in the intestinal tract of poultry by paratyphoid salmonella, with the mixtures being substantially free of pathogens.

The site of injection of the bacterial culture is preferably within either the region defined by the amnion, including the amniotic fluid and the embryo itself, the yolk sac, or the air cell. Most preferably, the bacterial culture is deposited in the air cell. The air cell is positioned at the large end of the egg adjacent the shell itself, and can be conveniently accessed by a shallow injection into the top of the large end of the egg. By the beginning of the fourth quarter of incubation, the amnion is sufficiently enlarged that penetration thereof is assured nearly all of the time when the injection is made from the center of the large end of the egg along the longitudinal axis.

The mechanism of injection is not critical, but it is preferred that the method not unduly damage the tissues and organs of the embryo or the extraembryonic membranes surrounding it so that the treatment will not decrease hatch rate. A hypodermic syringe fitted with a needle of about No. 22 gauge is suitable for the purpose. To inject into the air cell, the needle need only be inserted into the egg from just inside the inner surface of the egg to about seven millimeters within the shell. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria.

It is envisioned that a high speed automated injection system for avian embryos will be particularly suitable for practicing the present invention. Numerous such devices are available, exemplary being those disclosed in U.S. Pat. Nos. 4,040,388, 4,469,047 and 4,593,646, all to Miller, the disclosures of which are incorporated herein by reference. All such devices, as adapted for practicing the present invention, comprise an injector, the injector containing an injection liquid, the injection liquid containing a bacterial culture as described herein, with the injector positioned to inject an egg carried by the apparatus with the bacterial culture. Other features of the apparatus are discussed above. In addition, if desired, a sealing apparatus connected to the supporting frame and operatively associated with the injection apparatus may be provided for sealing the hole in the egg after injection thereof with a suitable sealing material.

A preferred apparatus for practicing the present invention is disclosed in European Patent Application No. 87305746.7 to Embrex, Inc., filed 29 June 1987. This device comprises an injection apparatus for delivering fluid substances into a plurality of eggs and suction apparatus (serving as the egg holder) which simultaneously engages and lifts a plurality of individual eggs from their upwardly facing portions and cooperates with the injection apparatus for injecting the eggs while the eggs are engaged by the suction apparatus. The features of this apparatus may be combined with the features of the apparatus described above for practicing the present invention.

The following examples are provided to more fully illustrate the present invention, and are not to be taken as restrictive thereof.

EXAMPLE 1

Preparation of CE Culture

Ceca and cecal material obtained from a salmonellae-negative adult chicken were anaerobically cultured in VL broth for 48 hours at 37° C. VL Broth is prepared by standard procedures. See, e.g., Pivnick et al., *J. Food prot.* 44, 909 (1981). The culture so produced is referred to as undiluted, undefined CE culture. As indicated below, dilutions of CE were made in sterile physiological saline.

EXAMPLE 2

Administration of CE Culture In Ovo

For the CE in ovo procedure, an 18 gauge needle was used to puncture a small hole in the large end (the air cell end) of fertile eggs which had been incubated for 18 days. Next, using a sterile syringe and a 22 gauge needle, 0.1 ml of the appropriately diluted CE was delivered through the hole into the air cell. The eggs were then put in a hatching cabinet (60% humidity, 37° C.) and held there until hatch on day 21. On the day of hatch, chicks were orally challenged with the indicated level of *Salmonella typhimurium*. Treatment groups of chicks were held in isolation units and given water and unmedicated broiler starter feed ad libitum. After seven days chicks were killed and the ceca semi-quantitatively analyzed for the presence of the test Salmonella.

The resistance of day-of-hatch broiler chicks to a $10^6$ *S. typhimurium* challenge following an *in ovo* injection of competitive exclusion bacteria on the 18th day of incubation is given in Table 1 below.

TABLE 1

| Treatment | Positives | CF | PF |
|---|---|---|---|
| Untreated | 11/12 | 2.9 | |
| Air Cell (T)[1] | 0/4 | 0 | >100 |
| Air Cell (M)[2] | 4/5 | 2.5 | 1 |
| Amnion (M)[3] | 2/2 | 2.1 | 1 |

[1]Air Cell was the site of injection and the 48 hour VL broth was diluted 1:1,000.
[2]Air Cell was the site of injection and the 48 hour VL broth was diluted 1:1,000,000.
[3]Amnion was the site of injection and the 48 hour VL broth was diluted 1:1,000,000.
CF - Colonization Factor is the mean Salmonella count per gram of ceca and cecal material for a treatment group.
PF - Protection Factor is the CF of the control group divided by the CF of the treatment group.

Eleven of the twelve untreated pips were colonized with a $10^6$ oral challenge on day-of-hatch, while none of the four air cell(T) chicks were colonized with the same challenge. The PF of 100 means that the treated chicks were greater than 100 times more resistant to *S. typhimurium* than the untreated chicks. The air cell (M) and amnion (M) treatments did not produce chicks more resistant than the untreated controls.

EXAMPLE 3

Administration of CE Culture In Ovo

Following the experiment described in Example 2 above, the resistance of day-old chicks to varying levels of an oral challenge with *S. typhimurium* following injection of competitive exclusion bacteria in ovo on the 18th day of incubation in accordance with the same procedures given in Example 2 above, was tested. Data for direct streaks of cecal samples from these birds are given in Table 2 below.

TABLE 2

| | Challenge Level | | | |
|---|---|---|---|---|
| Treatment | $10^1$ | $10^3$ | $10^5$ | $10^7$ |
| Control | 6/8[3] | 7/8 | 4/4 | 6/6 |
| Air Cell (T)[1] | 1/8 | 0/8 | 0/7 | 4/8 |
| Air Cell (M)[2] | 0/8 | 4/6 | 7/8 | 7/8 |

[1]Air Cell was the site of injection and the 48 hour VL broth was diluted 1:1,000.
[2]Air Cell was the site of injection and the 48 hour VL broth was diluted 1:1,000,000.
[3]Number of positive carriers of Salmonella per number of chickens analyzed.

When chicks were orally challenged with between $10^1$ and $10^7$ cells of *S. typhimurium*, untreated control chicks were readily colonized, even with only ten cells of Salmonella. When the CE was diluted 1:1,000,000, challenge levels over ten cells per bird colonized most of the chicks. However, when the chicks were treated with CE at the 1:1,000 dilution, the chicks were considerably less susceptible to colonization than controls. No birds at the $10^5$ and only half of the birds at the $10^7$ challenge level were colonized.

EXAMPLE 4

Effect of In Ovo CE Culture Administration on Hatchability

Following the experiments of Example 2 above, the hatchability, livability and body weight of chicks administered CE on day 18 of incubation in either the air cell or amnion was investigated. These data are given in Table 3 below.

TABLE 3

| In Ovo Treatment | Hatchability (%) | | | Livability (%) | | Body Weight (g) | |
|---|---|---|---|---|---|---|---|
| | [1]n | [2]Normal | Total | [4]n | [5]Live | [6]n | x ± S.D. |
| Noninjected | 100 | 96 | 96 | 10 | 100 | 10 | 292 ± 22 |
| Undiluted CE [7]Day 18 Aircell | 100 | 56 | 64 | 10 | 80 | 8 | 265 ± 48 |
| [8]1:1,000 Diluted CE Day 18 Aircell | 100 | 81 | 82 | 10 | 100 | 10 | 269 ± 38 |
| 1:1,000,000 Diluted CE Day 18 Aircell | 100 | 78 | 81 | 10 | 100 | 10 | 283 ± 24 |
| Undiluted CE Day 18 Amnion | 100 | 0 | 0 | — | — | — | — |
| 1:1,000 Diluted CE Day 18 Amnion | 100 | 0 | 0 | — | — | — | — |
| 1:1,000,000 Diluted CE Day 18 Amnion | 100 | 44 | 48 | 10 | 70 | 7 | 290 ± 28 |

[1]n = Number of eggs treated.
[2]Normal = Hatched normal chicks.
[3]Total = Hatched normal chicks + hatched dead chicks.
[4]n = Initial number of chicks brooded.
[5]Live = Percentage live at day 10 posthatch.
[6]n = Number of chicks weighed.
[7]Day 18 Undiluted = 18th day of incubation.
[8]Day 18 Diluted = Diluted in CEVA Laboratories Herpes Virus of Turkeys (HVT) vaccine diluent.

These data show that when an undiluted CE culture was placed in the Air Cell, hatchability was significantly reduced when compared to controls. However, when the CE culture was diluted 1:1,000 or greater, the hatchability and livability approached commercial acceptability. Putting the CE culture into the amnion, even at a 1:1,000,000 dilution, killed most of the chicks before hatch. For all treatments, the livability and body weight of chicks that hatched was not significantly affected by the CE treatment.

The foregoing material is illustrative of the present invention, and is not to be taken as restrictive thereof. The invention is defined by the following claims, with equivalents of the claims to be included therein.

That which is claimed is:

1. A method of introducing viable bacteria into the digestive tract of a bird so as to prevent Salmonella infection comprising administering to the region of the air cell of an egg which contains a viable embryonic bird, a viable unattenuated probiotic bacterial culture obtained form the caecum or large intestine of the digestive tracts of mature birds which are free of Salmonella in an amount effective to colonize the digestive tract of the embryonic bird contained within said fertilized bird egg which is selected from the group consisting of chicken, turkey, duck, goose, quail, and pheasant egg.

2. A method according to claim 1, wherein said administering step is followed by the step of incubating said bird egg to hatch.

3. A method according to claim 1, wherein said bird egg is selected from the class consisting of chicken and turkey eggs.

4. A method according to claim 1, wherein said bacterial culture is administered to said bird egg during about the final quarter of incubation.

5. A method according to claim 1, wherein said bird egg is a chicken egg and said bacterial culture is administered to said egg during about the egg's eighteenth day of incubation.

6. A method according to claim 1, wherein said bacterial culture is administered in combination with an oxygen scavenging agent.

7. A method according to claim 1, wherein said bacterial culture is a Salmonella competitive exclusion culture.

* * * * *